United States Patent [19]

Moldawer et al.

[11] Patent Number: 6,086,868
[45] Date of Patent: *Jul. 11, 2000

[54] METHOD FOR TREATING OR PREVENTING ISCHEMIA-REPERFUSION INJURY

[75] Inventors: Lyle L. Moldawer; James M. Seeger, both of Gainesville, Fla.; Timothy R. S. Harward, Santa Ana, Calif.; Satwant K. Narula, West Caldwell, N.J.

[73] Assignee: Schering Corporation, Kenilworth, N.J.

[ * ] Notice: This patent issued on a continued prosecution application filed under 37 CFR 1.53(d), and is subject to the twenty year patent term provisions of 35 U.S.C. 154(a)(2).

[21] Appl. No.: 08/846,378

[22] Filed: Apr. 30, 1997

Related U.S. Application Data

[60] Provisional application No. 60/016,746, May 2, 1996.

[51] Int. Cl.[7] .................................................... A61K 45/05
[52] U.S. Cl. ........................ 424/85.2; 424/85.1; 424/85.2
[58] Field of Search .................................. 424/85.1, 85.2

[56] References Cited

FOREIGN PATENT DOCUMENTS

WO 96/01318  1/1996  WIPO .

OTHER PUBLICATIONS

Hess et al., "Exogenous Il–10 suppresses tumor necrosis factor (TNF) dependent pulmonary neutrophil infiltration in a mouse model of visceral ischemia–reperfusion injury," *European Cytokine Network*, vol. 7, No. 2, p. 294, abstract 217 (Jun., 1996).

Eppinger et al., "Regulatory effects of interleukin–10 on lung ischemia–reperfusion injury," *Journal of Thoracic and Cardiovascular Surgery*, vol. 112, No. 5, pp. 1301–1306 (Nov. 1996).

Bean et al., 1993, *Infection and Immunity*, 61(11): 4937–39.

Caty et al., 1990, *Ann., Surg.*, 212(6):694–99.

Colletti et al., 1990, *J. Clin. Invest.*, 85:1936–43.

Eppinger et al., 1995, *Surgical Forum*, 306–308 (Abstract).

Gerard et al., 1993 *J. Exp. Med.*, 177:547–50.

Moore et al., 1993, *Annu. Rev. Immunol.*, 11:165–90.

Roumen et al., 1993, *Annals of Surgery*, 218(6):769–76.

Seekamp et al., 1993, *Am. J. Pathology*, 143(2):453–63.

van der Poll et al., 1995, *J. Immunol.*, 155:5397–5401.

Welborn et al., 1996, *Shock*, 6(3):171–76.

Welbourn et al., 1991, *J. Appl. Physiol.* 70:2645–49.

Sawa et al, *European Heart Journal*, 1994, 15:471, Abstr. No. P2501.

Connolly, et al., *Transplant Proc.*, 1995, 27(5):2816–18.

*Primary Examiner*—Nita Minnifield
*Assistant Examiner*—Padma Baskar
*Attorney, Agent, or Firm*—David B. Schram

[57] ABSTRACT

There is disclosed a method of treating ischemia-reperfusion injury comprising administering an effective amount of Interleukin-10 to a patient suffering or expected to suffer from such injury.

27 Claims, 6 Drawing Sheets

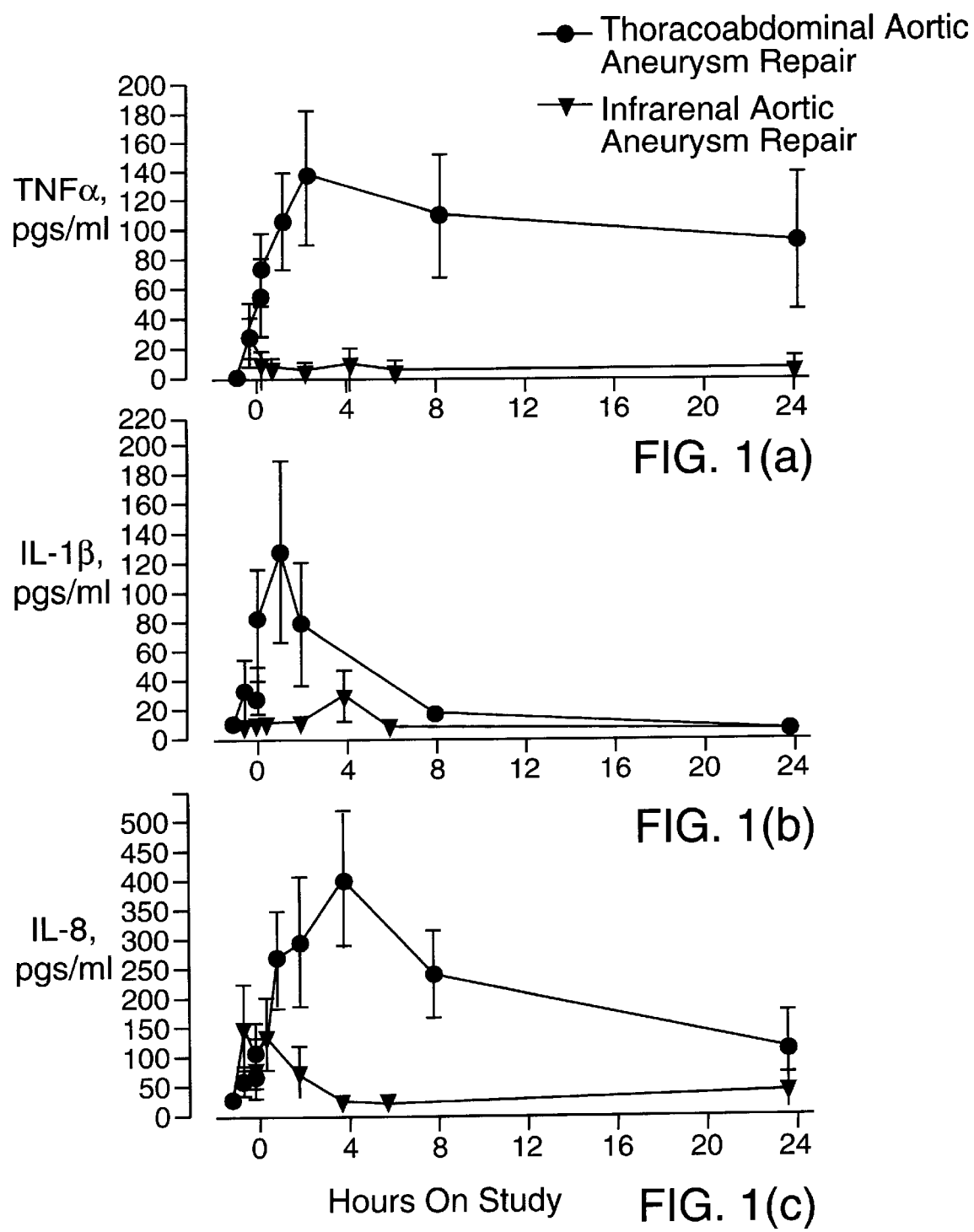

METHOD FOR TREATING OR PREVENTING ISCHEMIA-REPERFUSION INJURY

This application claims priority to U.S. provisional application No. 60/016,746, filed May 2, 1996.

BACKGROUND OF THE INVENTION

Ischemia-reperfusion injury frequently occurs when the flow of blood to a region of the body is temporarily halted (ischemia) and then re-established (reperfusion). Ischemia-reperfusion injury can occur during certain surgical procedures, such as repair of certain aortic aneurysms and organ transplantation. Clinically ischemia-reperfusion injury in manifested by such complications as pulmonary dysfunction, including adult respiratory distress syndrome, renal dysfunction, consumptive coagulopathies including thrombocytopenia, fibrin deposition into the microvasculature and disseminated intravascular coagulopathy, transient and permanent spinal cord injury, cardiac arrhythmias and acute ischemic events, hepatic dysfunction including acute hepatocellular damage and necrosis, gastrointestinal dysfunction including hemorrhage and/or infarction and multisystem organ dysfunction (MSOD) or acute systemic inflammatory distress syndromes (SIRS). The injury may occur in the parts of the body to which the blood supply was interrupted, or it can occur in parts fully supplied with blood during the period of ischemia.

International Patent Publication No. WO 96/01318 relates to polypeptides other than interleukin-10 (IL-10) allegedly having one or more properties similar to those of IL-10. Among the very long list of diseases allegedly treatable with these non-IL-10 proteins are tissue damage as a result of "hypoxia/ischemia (infarction: reperfusion)", "ischemia", "reperfusion injury", and "reperfusion syndrome". However, there is no evidence in this publication that the non-IL-10 proteins would actually work for treating all of the diseases in the long list.

SUMMARY OF THE INVENTION

The present invention comprises a method for treating ischemia-reperfusion injury comprising administering to a patient in need of such treatment an effective amount of IL-10. Another aspect of this invention comprises a method for preventing ischemia-reperfusion injury in a patient about to undergo a procedure capable of causing ischemia-reperfusion injury or to a patient who has already undergone such procedure in which ischemia-reperfusion injury has not yet occurred comprising administering to the patient an effective amount of IL-10.

Preferred applications of this invention are preventing ischemia reperfusion injury by administering the IL-10 in conjunction with surgical repair of the thoracic or suprarenal aorta due to aneurysmal disease, but also in conjunction with those surgical procedures that induce or require transient occlusion or bypass of the visceral blood supply via the hepatic, renal and/or enteric arteries secondary to major organ transplant, including liver, kidney, small intestine, and pancreas as well as surgical procedures that result in the transient reduction or prevention of blood flow to the viscera including hepatic and biliary surgical resections, total or partial pancreatectomy (Whipple procedure), total and partial gastrectomy, esophagectomy, colorectal surgery, vascular surgery for mesenteric vascular disease, or abdominal insufflation during laparoscopic surgical procedures. Additional applications include blunt or penetrating trauma that results in interruption of blood flow to the viceral organs including those arising from penetrating wounds to the abdomen resulting from gun shot wounds, stab wounds or from penetrating wounds or blunt abdominal trauma secondary to deacceleration injury and/or motor vehicle accidents. Other preferred applications include diseases or procedures that result in systemic hypotension that either disrupts or decreases the flow of blood to the visceral organs, including hemorrhagic shock due to blood loss, cardiogenic shock due to myocardial infarction or cardiac failure, neurogenic shock or anaphylaxis.

The amount of IL-10 to be administered is preferably between 0.1 to 500 $\mu$g/kg of body weight, more preferably 1 to 50 $\mu$g/kg. The IL-10 may be of human or viral origin produced biologically from mammalian cellular sources or by recombinant DNA technology. Administration preferably takes place by intravenous, intramuscular or subcutaneous injection. The IL-10 is preferably administered from one to zero hours before the blood flow is reestablished.

In those surgical procedures in which temporary or sustained disruption of blood flow is anticipated to occur, as before surgical repair of thoracoabdominal or supraceliac aneursymal disease, or surgical procedures to the abdomen that will necessarily include the transient reduction in visceral blood flow, or for organ transplantation, the IL-10 is preferably given either as a single bolus injection one to zero hours before the ischemic event or as a continuous intravenous injection beginning one to zero hours before the ischemic event and extending during the perioperative period and continuing for at least eight hours after restoration of visceral blood flow. For individuals in whom disrupted visceral blood flow has already occurred, as in those individuals with trauma or injury to the visceral organs or their blood supply, or in patients with systemic hypotension due to shock, the IL-10 would be preferably given either as a single bolus injection prior to or simultaneously with restoration of normal visceral blood flow or as a continuous intravenous injection prior to or simultaneously with restoration of normal visceral blood flow and extending for at least eight hours after restoration of visceral blood flow.

Alternatively the IL-10 may be administered by gene therapy or transfer using either liposomes and mammalian expression plasmids, mechanical delivery systems (gene gun) of viral transfection schemes, including but not limited to adenovirus, adeno-associated virus, retrovirus or herpes simplex virus constructs.

BRIEF DESCRIPTION OF THE DRAWINGS

FIG. 1 illustrates the plasma TNF-$\alpha$, IL-1$\beta$ and IL-8 concentrations following thoracoabdominal and infrarenal aortic aneurysm repair.

DETAILED DESCRIPTION OF THE INVENTION

Figures 2A, 2B, 2C:
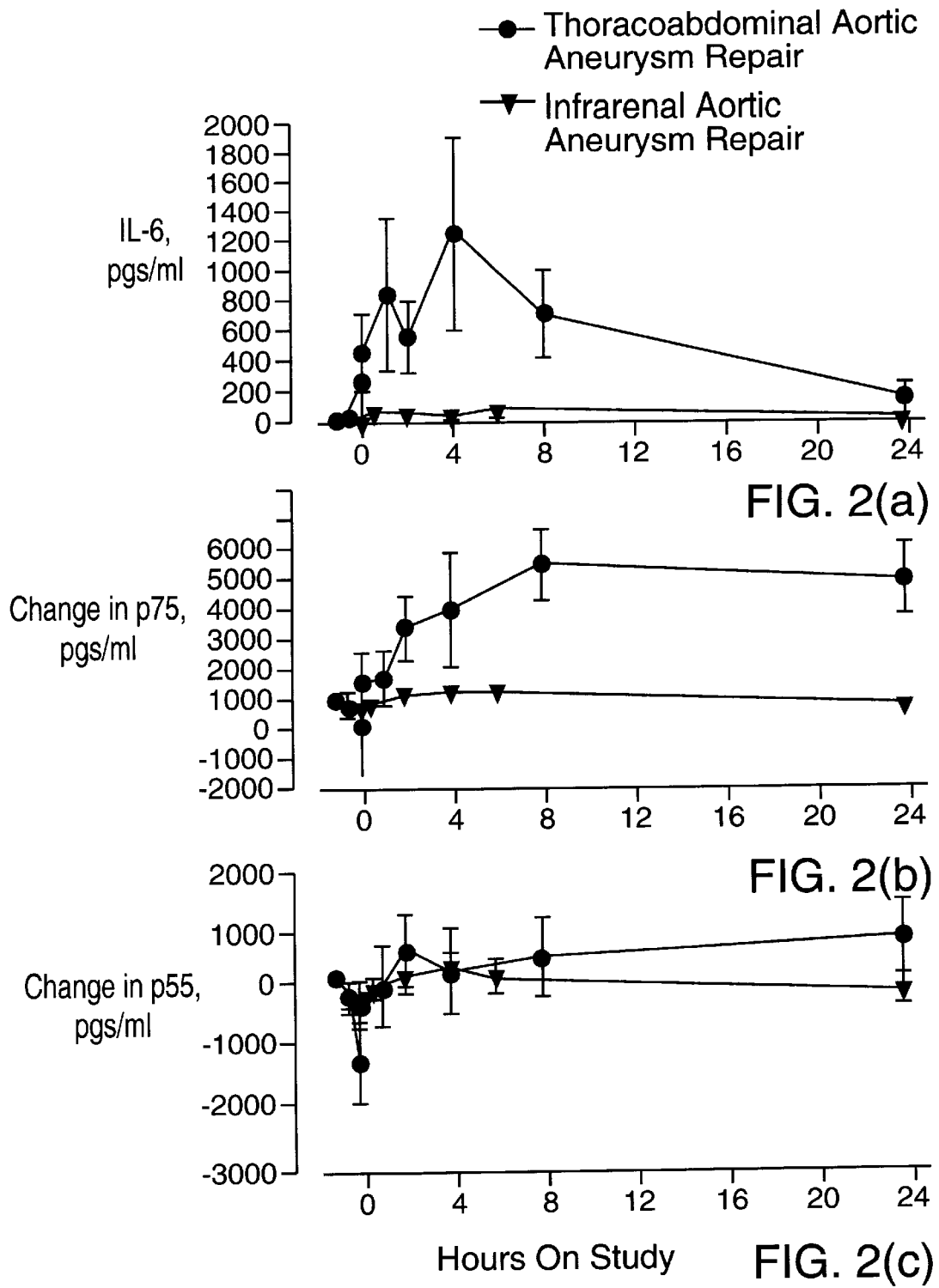
FIG. 2 illustrates the plasma IL-6 and changes in plasma p55 and p75 concentrations following thoracoabdominal and infrarenal aortic aneurysm repair.

As used herein, "interleukin-10" or "IL-10" is defined as a protein which (a) has an amino acid sequence of mature IL-10 (e.g., lacking a secretory leader sequence) as disclosed in U.S. Pat. No. 5,231,012 and (b) has biological activity that is common to native IL-10. Also included are muteins and other analogs, including the Epstein-Barr Virus protein BCRF1 (viral IL-10), which retain the biological activity of IL-10.

IL-10 suitable for use in the invention can be obtained from culture medium conditioned by activated cells secreting the protein, and purified by standard methods. Additionally, the IL-10, or active fragments thereof, can be chemically synthesized using standard techniques known in the art. See Merrifield, *Science* 233:341 (1986) and Atherton et al., *Solid Phase Peptide Synthesis: A Practical Approach*, 1989, I.R.L. Press, Oxford. See also U.S. Pat. No. 5,231,012.

Preferably, the protein or polypeptide is obtained by recombinant techniques using isolated nucleic acid encoding the IL-10 polypeptide. General methods of molecular biology are described, e.g., by Sambrook et al., *Molecular Cloning, A Laboratory Manual*, Cold Spring Harbor, N.Y., 2d ed., 1989, and by Ausubel et al., (eds.) *Current Protocols in Molecular Biology*, Green/Woley, New York (1987 and periodic supplements). The appropriate sequences can be obtained using standard techniques from either genomic or cDNA libraries. Polymerase chain reaction (PCR) techniques can be used. See, e.g., *PCR Protocols: A Guide to Methods and Applications*, 1990, Innis et al., (Ed.), Academic Press, New York, N.Y.

Libraries are constructed from nucleic acid extracted from appropriate cells. See, e.g., U.S. Pat. No. 5,231,012, which discloses recombinant methods for making IL-10. Useful gene sequences can be found, e.g., in various sequence databases, e.g., GenBank and BMPL or nucleic acid and PIR and Swiss-Prot for protein, c/o Intelligenetics, Mountain View, Calif., or the Genetics Computer Group, University of Wisconsin Biotechnology Center, Madison, Wis.

Clones comprising sequences that encode human IL-10 have been deposited with the American Type Culture Collection (ATCC), Manassas, Va., under Accession Nos. 68191 and 68192. Identification of other clones harboring the sequences encoding IL-10 is performed by either nucleic acid hybridization or immunological detection of the encoded protein, if an expression vector is used. Oligonucleotide probes based on the deposited sequences disclosed in U.S. Pat. No. 5,231,012 are particularly useful. Oligonucleotide probes sequences can also be prepared from conserved regions of related genes in other species. Alternatively, degenerate probes based on the amino acid sequences of IL-10 can be used.

Standard methods can be used to produce transformed prokaryotic, mammalian, yeast or insect cell lines which express large quantities of the polypeptide. Exemplary *E. coli* strains suitable for both expression and cloning include W3110 (ATCC Bi, 27325), X1776 (ATCC No. 31244). X2282, and RR1 (ATCC Mp/31343). Exemplary mammalian cell lines include COS-7 cells, mouse L cells and CHP cells. See Sambrook (1989), supra and Ausubel et al., 1987 supplements, supra.

Various expression vectors can be used to express DNA encoding IL-10. Conventional vectors used for expression of recombinant proteins in prokaryotic or eukaryotic cells may be used. Preferred vectors include the pcD vectors described by Okayama et al., Mol. Cell. Biol. 3:280 (1983); and Takebe et al., Mol. Cell. Biol. 8:466 (1988). Other SV40-based mammalian expression vectors include those disclosed in Kaufman et al., Mol. Cell. Biol. 2:1304 (1982) and U.S. Pat. No. 4,675,285. These SV40-based vectors are particularly useful in COS-7 monkey cells (ATCC No. CRL 1651), as well as in other mammalian cells such as mouse L cells. See also, Pouwels et al., (1989 and supplements) *Cloning Vectors: A Laboratory Manual*, Elsevier, N.Y.

The IL-10 may be produced in soluble form, such as a secreted product of transformed or transfected yeast, insect or mammalian cells. The peptides can then be purified by standard procedures that are known in the art. For example, purification steps could include ammonium sulfate precipitation, ion exchange chromatography, gel filtration, electrophoresis, affinity chromatography, and the like. See *Methods in Enzymology Purification Principles and Practices* (Springer-Verlag, N.Y., 1982).

Alternatively, IL-10 may be produced in insoluble form, such as aggregates or inclusion bodies. The IL-10 in such a form is purified by standard procedures that are well known in the art. Examples of purification steps include separating the inclusion bodies from disrupted host cells by centrifugation, and then solubilizing the inclusion bodies with chaotropic agent and reducing agent so that the peptide assumes a biologically active conformation. For specifics of these procedures, see, e.g. Winkler et al., Biochemistry 25:4041 (1986), Winkler et al., Bio/Technology 3:9923 (1985); Koths et al., and U.S. Pat. No. 4,569,790.

The nucleotide sequences used to transfect the host cells can be modified using standard techniques to make IL-10 or fragments thereof with a variety of desired properties. Such modified IL-10 can vary from the naturally-occurring sequences at the primary structure level, e.g., by amino acid, insertions, substitutions, deletions and fusions. These modifications can be used in a number of combinations to produce the final modified protein chain.

The amino acid sequence variants can be prepared with various objectives in mind, including increasing serum half-life, facilitating purification or preparation, improving therapeutic efficacy, and lessening the severity or occurrence of side effects during therapeutic use. The amino acid sequence variants are usually predetermined variants not found in nature, although others may be post-translational variants. Such variants can be used in this invention as long as they retain the biological activity of IL-10.

Modifications of the sequences encoding the polypeptides may be readily accomplished by a variety of techniques, such as site-directed mutagenesis (Gillman et al., Gene 8:81 (1987)). Most modifications are evaluated by routine screening in a suitable assay for the desired characteristics. For instance, U.S. Pat. No. 5,231,012 describes a number of in vitro assays suitable for measuring IL-10 activity.

Preferably, human IL-10 is used for the treatment of humans, although viral IL-10 could possibly be used. Most preferably, the IL-10 used is recombinant human IL-10. The preparation of human IL-10 has been described in U.S. Pat. No. 5,231,012. The cloning and expression of viral IL-10 (BCRF1 protein) from Epstein-Barr virus has been disclosed by Moore et al., Science 248:1230 (1990).

For examples of procedures and assays to determine IL-10 activity, see U.S. Pat. No. 5,231,012. This patent also provides proteins having IL-10 activity and production of such proteins including recombinant and synthetic techniques.

To prepare pharmaceutical compositions of IL-10 for practice of this invention, the IL-10 is admixed with a pharmaceutically acceptable carrier or excipient which is preferably inert. A pharmaceutical carrier can be any compatible non-toxic substance suitable for delivery of the polypeptide to a patient. Preparation of such pharmaceutical compositions is known in the art; see, e.g., *Remington's Pharmaceutical Sciences, and U.S. Pharmacopeia: National Formulary*, Mack Publishing Company, Easton, Pa. (1984).

Compositions may be ingested orally or injected into the body. Formulations for oral use include compounds to protect the polypeptides from proteases which occur in the gastrointestinal tract. Injections are usually intramuscular, subcutaneous, intradermal or intravenous. Alternatively, intra-articular injection or other routes could be used in appropriate circumstances.

When administered parenterally, the compositions can be formulated in a unit dosage injectable form (solution, suspension, emulsion) in association with a pharmaceutical carrier. For instance, the IL-10 may be administered in aqueous vehicles such as water, saline or buffered vehicles with or without various additives and/or diluting agents. Examples of suitable carriers are normal saline, Ringer's solution, dextrose solution, and Hank's solution. Non-aqueous carriers such as fixed oils and ethyl oleate may also be used. A preferred carrier is 5% dextrose/saline. The carrier may contain minor amounts of additives such as substances that enhance isotonicity and chemical stability, e.g., buffers and preservatives. However, the IL-10 in the composition is preferably formulated in purified form substantially free of aggregates and other proteins. In addition, it should be noted that a suspension, such as a zinc suspension, can be prepared to include the polypeptide. Such a suspension can be useful for subcutaneous (SQ) or intramuscular (IM) injection.

It is believed that ischemia-reperfusion injury is caused, at least in part, by the release of excess amounts of proinflammatory cytokines, such as TNF-$\alpha$, IL-1, IL-6, and IL-8. Examples 1 and 2 were performed to test this theory and the effect IL-10 has on ischemic-reperfusion injury.

EXAMPLE 1

Initial studies investigated prospectively the associative relationship between the proinflammatory cytokine response and morbidity and mortality following visceral ischemia and reperfusion in humans by measuring proinflammatory cytokine levels in patients undergoing thoracoabdominal or infrarenal aortic aneurysm repair, and comparing these results to the incidence of postoperative organ dysfunction.

Sixteen human patients undergoing elective repair of a thoracoabdominal aortic aneurysm and 9 patients undergoing elective infrarenal aortic aneurysm repair agreed to arterial blood sampling for proinflammatory cytokine measurements. Each thoracoabdominal aortic aneurysm was repaired through a left flank incision using a retroperitoneal approach. The diaphragm was divided circumferentially, allowing exposure of the descending thoracic aorta. Prior to cross-clamping, each patient was given mannitol (0.5 gm/kg) and solumedrol (15 mg/kg). Depending upon the location of the aneurysm, the visceral arteries were sewn onto the graft as a Carrel patch or as part of the proximal anastomosis with an extensive posterior taper to the graft. Once the repair was completed, coagulation products (platelets and fresh frozen plasma) were infused as needed. Preoperatively, a catheter was placed in the lumbar spinal column and cerebrospinal fluid drained to maintain intrathecal pressure at 5–10 cm water. Infrarenal abdominal aortic aneurysms were repaired transperitoneally using standard surgical techniques and the aorta was reconstructed using either a straight tube graft to the aortic bifurcation or a bifurcated graft to the internal/external iliac artery bifurcation.

In both groups of patients, arterial blood samples (7 ml) were obtained following induction of anesthesia, just prior to aortic cross-clamp placement, just prior to clamp release, and at timed intervals (1, 2, 4, 6 to 8, 24 hrs and daily for 7 days) after reperfusion. Clinical and laboratory data were collected prospectively from all patients to determine preoperative risk factors and postoperative organ dysfunction patterns. Data collected included operative parameters (total operative time, aortic cross-clamp time, estimated blood loss, intraoperative complications), postoperative course (complications, organ dysfunction) and causes of death. Laboratory values were analyzed during the initial 7 postoperative days to focus on the injury associated with tissue ischemia-reperfusion after thoracoabdominal and infrarenal aortic aneurysm repair.

Postoperative pulmonary dysfunction was defined as the need for positive-pressure mechanical ventilatory assistance for greater than 7 days while postoperative hepatic dysfunction was defined as peak lactate dehydrogenase (LDH) levels greater than 500 U/L and either serum transaminase levels (AST/ALT) greater than 200 U/L or an increase in total bilirubin levels greater than 3 mg/dl. Renal dysfunction was defined as an increase in serum creatinine of 2 mg/dl or more over preoperative baseline, while a platelet count less than 50,000/mm$^3$ or a drop in white blood cell count below 4,500/mm$^3$ indicated the presence of hematopoietic dysfunction. Patients with 2 or more organ systems meeting these criteria were designated as having multiple system organ dysfunction [MSOD].

Freshly thawed plasma samples were assayed for TNF-$\alpha$, IL-1, IL-6, IL-8 and TNF-$\alpha$shed receptors (p55 and p75) by ELISA. The sensitivity of the TNF-$\alpha$, IL-1, IL-6, IL-8, p55 and p75 assays are 14, 10, 27, 313, 14 and 17 pg/ml, respectively.

The mortality and morbidity data from the 16 patients undergoing thoracoabdominal aortic aneurysm repair and the 9 patients undergoing infrarenal aortic aneurysm repair are reported in Table I.

TABLE 1

Incidence of organ dysfunction following thoracoabdominal or infrarenal aortic aneurysm repair.

Data presented shows that the frequency of pulmonary dysfunction and MSOD following thoracoabdominal aortic aneurysm repair was significantly higher than following abdominal aortic aneurysm repair.

|  | Thoracoabdominal Aortic Aneurysm (n = 16) | Infrarenal Aortic Aneurysm (n = 9) |
| --- | --- | --- |
| Mortality | 19% | 0% |
| Pulmonary Dysfunction | 56%* | 11% |

-continued

|  | Thoracoabdominal Aortic Aneurysm (n = 16) | Infrarenal Aortic Aneurysm (n = 9) |
| --- | --- | --- |
| Tracheostomy | 25% | 0% |
| Renal Dysfunction | 38%** | 0% |
| Dialysis | 13% | 0% |
| Hepatic Dysfunction | 31% | 0% |
| Hematopoietic Dysfunction | 38%** | 0% |
| Leukopenia | 13% | 0% |
| MSOD | 44%* | 0% |

*p < 0.05 by Fisher's exact test
**p = 0.057 by Fisher's exact test

Three patients died after thoracoabdominal aortic aneurysm repair, 2 from MSOD and 1 from cardiac arrest. Pulmonary dysfunction occurred in 9 patients and placement of a temporary tracheostomy was eventually required in 4 patients. Renal dysfunction developed in 6 patients and hemodialysis was necessary in 2 of them. Hepatic dysfunction, thrombocytopenia, and leukopenia developed after thoracoabdominal aortic aneurysm repair in 5, 6, and 2 patients, respectively, and lower extremity dysfunction due to spinal cord injury occurred in 2 patients. In contrast, there were no operative deaths after infrarenal aortic aneurysm repair (Table 1). Pulmonary dysfunction occurred in only 1 patient and there was no evidence of renal, hepatic, hematopoietic or lower extremity dysfunction in any patient.

The peak plasma cytokine responses in both groups of patients are reported in Table 2.

TABLE 2

Peak proinflammatory cytokine concentrations following thoracoabdominal or infrarenal aortic aneurysm repair.

Plasma samples were obtained 0,1, 2, 4, 6–8, 24, 48, 72 hours and daily for up to seven days following thoracoabdominal or infrarenal aortic aneurysm repair. Peak concentrations are reported here. Levels of all proinflammatory cytokines were significantly higher in patients following thoracoabdominal than infrarenal aortic aneurysm repair (p<0.05).

|  | Thoracoabdominal Aortic Aneurysm (n = 16) | Infrarenal Aortic Aneurysm (n = 9) |
| --- | --- | --- |
| TNF-α pgs/ml | 161 ± 58 | 10 ± 10 |
| IL-1b pgs/ml | 133 ± 59 | 24 ± 10 |
| IL-6, pgs/ml | 1,280 ± 664 | 181 ± 108 |
| IL-8, pgs/ml | 410 ± 139 | 137 ± 77 |
| p55, change from baseline in pgs/ml | 751 ± 668 | 204 ± 218 |
| p75, change from baseline in pgs/ml | 5,201 ± 1,983 | 383 ± 171 |
| C3a, µg/ml | 111 ± 21 | 30 ± 7 | all values are significantly different between the two groups, by two-way ANOVA, p < 0.05

Plasma TNF-α IL-1, IL-6 and IL-8 concentrations were undetectable prior to surgery. Following surgical repair of thoracoabdominal aortic aneurysms, a monophasic TNF-α response was detected in 11 of 16 patients (69%) (FIG. 1). TNF-α levels peaked 4 hours after reperfusion and then gradually decreased toward baseline over the next 24 hours. IL-6 and IL-8 levels also increased in a monophasic pattern with peak levels again occurring 4 hours after reperfusion in 16 (100%) and 11 (70%) patients, respectively; however, unlike the pattern seen with TNF-α, circulating IL-6 and IL-8 levels decreased to baseline within 8 hours. IL-1 was also detected in a monophasic pattern in 50% of the thoracoabdominal aortic aneurysm patients, but its peak levels occurred at 1 hour after reperfusion and IL-1 levels returned to baseline levels 4–6 hours after reperfusion. The plasma concentrations of the soluble TNF-α receptors, p55 and p75, were increased after thoracoabdominal aortic aneurysm repair in 12 (75%) and 16 (100%) of the patients assayed, respectively (FIG. 2). p55 receptor concentrations reached a zenith at 24 hours and remained elevated for several days while p75 receptor concentrations continued to increase throughout the initial 48 hours after reperfusion. In contrast to thoracoabdominal aortic aneurysm repair patients, peak serum levels of TNF-α, IL-1, IL-6, IL-8, p55 and p75 were 3 to 15-fold less in patients undergoing infrarenal abdominal aortic aneurysm repair (Table 2 and FIGS. 1 and 2).

A retrospective analysis was performed in an effort to establish an associative relationship between patient clinical outcome and the concentrations of various proinflammatory cytokines. Patients undergoing thoracoabdominal aortic aneurysm repair in whom peak TNF-α levels were less than 150 pg/ml did not experience single or multiple organ dysfunction, while single organ dysfunction and MSOD were common in patients whose peak TNF-α levels were greater than 150 pg/ml (Table 3).

TABLE 3

Relationship between post-operative organ dysfunction and peak circulating TNF-α levels.

|  | TNF-α < 150 pgs/ml | TNF-α > 150 pgs/ml |
| --- | --- | --- |
| Mortality | 1 death cardiac | 2 deaths - MSOD |
| Pulmonary Dysfunction | 0% | 57%** |
| Renal Dysfunction | 0% | 71%* |
| Dialysis | 0% | 29% |
| Hepatic Dysfunction | 0% | 71%* |
| Hematopoietic Dysfunction | 0% | 71%* |
| Leukopenia | 0% | 28% |
| MSOD | 0% | 86%* |

*p < 0.05 by Fisher's exact test
**p = 0.07 by Fisher's exact test

In addition, patients who developed MSOD after thoracoabdominal aortic aneurysm repair had higher circulating levels of all assayed cytokine and soluble TNF-α receptors (p55 and p75) as compared to patients without MSOD (Table 4); however, only TNF-α and p55 receptor levels were statistically different (p<0.05) while there was a trend toward higher levels of IL-1, IL-6, IL-8 and p75 receptors in patients who developed MSOD as compared to patients without MSOD (Table 4).

TABLE 4

Plasma proinflammatory cytokine concentrations in patients with and without evidence of multisystem organ dysfunction (MSOD).

Peak plasma concentrations of TNFα, IL-6, p55 and p75 were significantly higher in patients following thoracoabdominal aortic aneurysm repair with MSOD than in patients either following thoracoabdominal aortic aneurysm repair without MSOD or in patients following infrarenal aortic aneurysm repair.

|  | Thoracoabdominal Aortic Repair with MSOD | Thoracoabdominal Aortic Repair w/o MSOD | Infrarenal Aortic Repair |
|---|---|---|---|
| cross-clamp time | 56 ± 5 mins | 33 ± 4 mins | nr |
| TNFα | 414 ± 59* | 86 ± 55 | 10 ± 10 |
| IL-1β | 173 ± 112 | 102 ± 62 | 24 ± 10 |
| IL-6 | 4,907 ± 1887* | 344 ± 66 | 181 ± 108 |
| IL-8 | 601 ± 259 | 376 ± 107 | 137 ± 77 |
| p55 | +3,515 ± 711* | +452 ± 415 | +204 ± 218 |
| p75 | +9,469 ± 1940* | +4,136 ± 1,884 | +382 ± 171 | values for p55 and p75 are changes from baseline. All values are in pgs/ml.
*$p < 0.05$ versus no MSOD by 2-way ANOVA
nr = not reported The results presented here demonstrate that surgical repair of thoracoabdominal aortic aneurysms which cause visceral ischemia-reperfusion injury results in a systemic proinflammatory cytokine response characterized by the appearance of TNF-α, IL-1, IL-6 and IL-8 in the blood as early as 1 to 4 hours after release of the cross-clamp. Additionally, the presence and magnitude of this proinflammatory cytokine response is associated with the incidence of postoperative organ dysfunction after thoracoabdominal aortic aneurysm repair.

Ischemia and subsequent reperfusion injury of the viscera appear to be critical for the induction of this systemic proinflammatory cytokine response, since the magnitude of the proinflammatory cytokine response is 3 to 15-fold less in patients undergoing repair of the infrarenal aorta than following thoracoabdominal aortic repair. In addition, patients having infrarenal aortic aneurysm repair, in whom visceral ischemia is avoided, have a significantly lower incidence of postoperative organ dysfunction.

To further explore the direct role of acute visceral ischemia in mediating this proinflammatory cytokine response and associated organ dysfunction, an additional 8 patients were studied following elective thoracoabdominal aortic aneurysm repair. However, in this case, duration of visceral ischemia was reduced by left atrial-femoral artery bypass (LAFBP) and retrograde perfusion of the visceral arteries. LAFBP provides distal blood flow during repair of thoracoabdominal aneurysms and reduces visceral ischemia time. We prospectively examined the effect of LAFBP on patients undergoing thoracoabdominal aortic repair (n=8) and compared the cytokine response, morbidity, and mortality to patients undergoing standard thoracoabdominal aortic aneurysm repair (n=16) without the benefit of LAFBP.

Timed measurement of cytokine levels was done during the 48 hour perioperative period and cytokine levels were measured by ELISA. Clinical data concerning postoperative pulmonary, hepatic, renal, and hematopoietic dysfunction were also prospectively collected. Patients undergoing repair of thoracoabdominal aortic aneurysms with LAFBP had shorter visceral ischemia times (18±5 min. vs 45±12 min.) and statistically significant reductions in circulating TNF-α, IL-10, and p75 levels ($p<0.05$ by two-way ANOVA) when compared to the control group (Table 5).

TABLE 5

Plasma proinflammatory cytokine concentrations in patients undergoing thoracoabdominal aortic aneurysm with left atrial femoral bypass (LAFB) or without LAFB.

Peak plasma concentrations of TNF-α, IL-10 and p75 were significantly higher in patients following thoracoabdominal aortic aneurysm repair without LAFB than in patients following thoracoabdominal aortic aneurysm repair with LAFB.

|  | Repair with LAFBP(n + 8) | Repair W/O LAFBP (n = 16) |
|---|---|---|
| TNF-α, pgs/ml | 10 ± 10 | 161 ± 58* |
| IL-6, pgs/ml | 2320 ± 1644 | 1280 ± 664 |
| IL-8, pgs/ml | 410 ± 139 | 458 ± 402 |
| IL-10, pgs/ml | 60 ± 29 | 806 ± 260* |
| p55, baseline pgs/ml | +741 ± 298 | +751 ± 668 |
| p75, baseline pgs/ml | +641 ± 406 | +5201 ± 1983* |

*$p < 0.05$

Additionally, the incidence of pulmonary dysfunction, renal dysfunction, thrombocytopenia, multisystem organ dysfunction, and mortality were reduced in patients undergoing LAFBP, although the numbers were too small to show any statistical difference.

These findings suggest that acute visceral ischemia-reperfusion injury secondary to thoracoabdominal aortic aneurysm repair is associated with a high rate of morbidity and multisystem organ dysfunction that is not seen with similar surgical procedures that do not cause visceral ischemia. Furthermore, techniques aimed at reducing the duration of ischemia during aortic cross-clamping (left atrial-femoral bypass) appear to reduce the magnitude of the TNF-α and IL-1 responses.

EXAMPLE 2

Experiments in mice have been conducted that demonstrate that pretreatment with recombinant human IL-10 can reduce distant organ injury in a clinically relevant model of acute visceral ischemia-reperfusion injury. The initial goal of these studies was to develop a clinically relevant model of acute ischemia-reperfusion injury that demonstrated evidence of organ injury that was dependent upon an endogenous proinflammatory cytokine response that could be inhibited by either a TNF-α receptor construct or a monoclonal antibody against the IL-1 type I (p80) receptor (35F5, Hoffmann-LaRoche, Nutley, N.J.).

Figure 3:
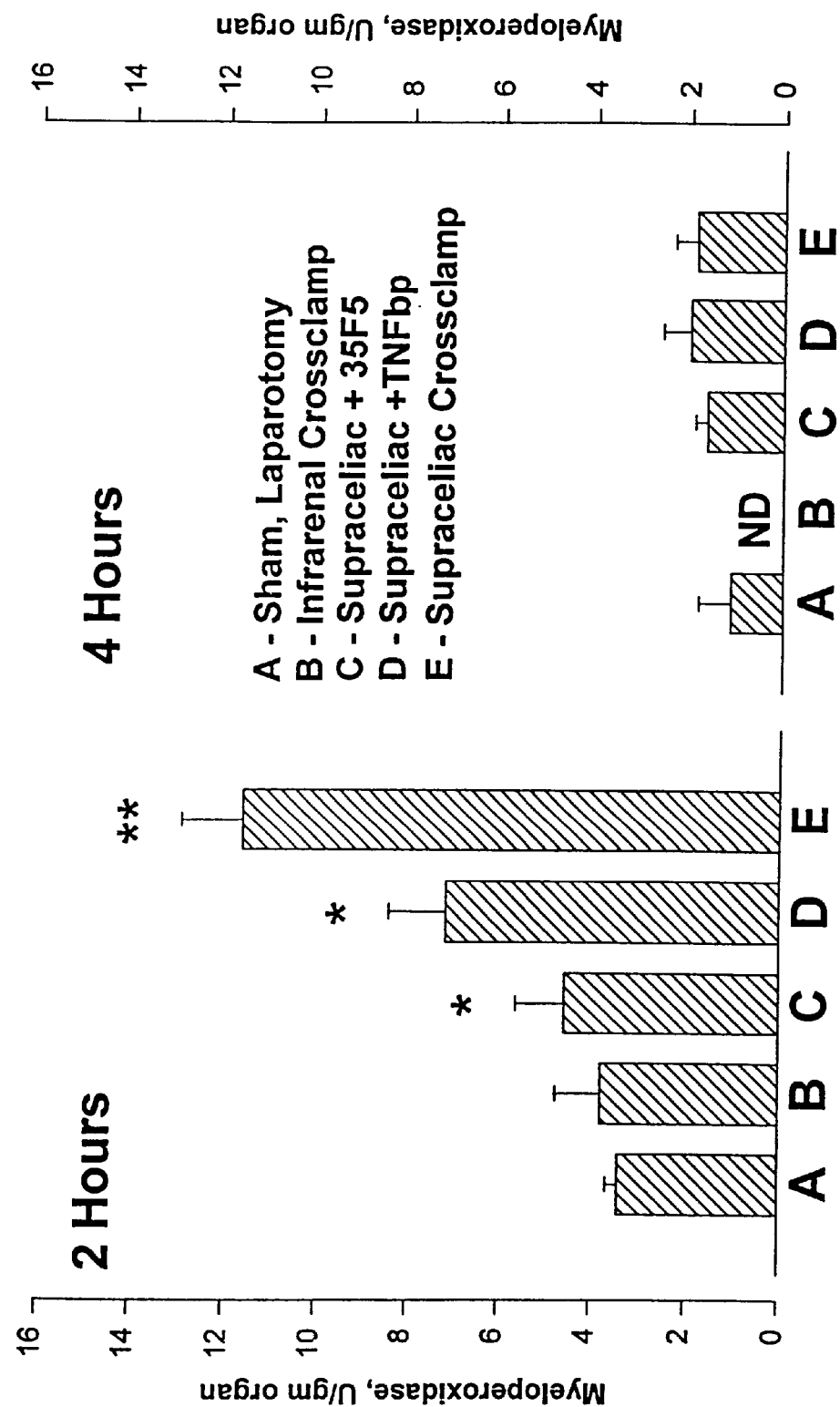
FIG. 3 illustrates the changes in lung myeloperoxidase levels (neutrophil infiltration) in mice following supraceliac aortic cross clamp and treatment with inhibitors of TNF and IL-1.

Thirty mice (C57BL6, approx. 20 gm) were anesthetized with pentobarbital. In 16 of these animals, the supraceliac aorta was cross-clamped for 30 minutes. Six animals had their infrarenal aorta cross-clamped for 30 minutes, while another 8 animals received only anesthesia, incision and bowel mobilization without aortic cross-clamping. Two hours prior to supraceliac aortic cross-clamping, 8 of the 16 animals were pretreated with the intraperitoneal injection of 10 mg/kg BW of TNF-bp (a TNF-α binding protein that is comprised of the extracellular domains of two p55 TNF-α receptors covalently linked to polyethylene glycol). Two hours after aortic clamp removal and abdominal wound closure, the animals were sacrificed and lung neutrophil infiltration was evaluated by MPO content. Results are shown in FIG. 3. Supraceliac aortic cross-clamping resulted in a significant increase in pulmonary neutrophil infiltration at 2 hours, which was not seen in animals that had the infrarenal aorta cross-clamped. Pretreatment of the animals undergoing supraceliac aortic cross-clamping with TNF-bp significantly attenuated this increase.

Figure 4:
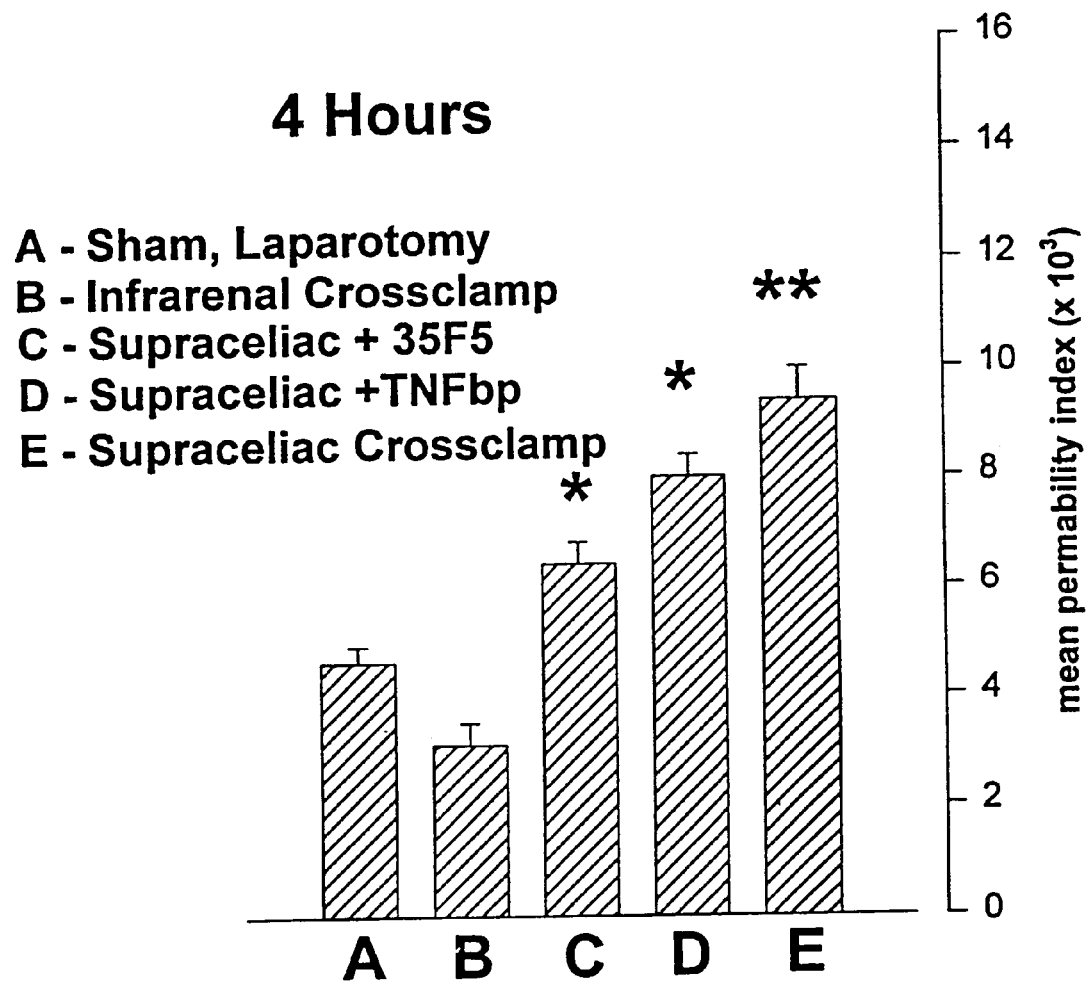
FIG. 4 illustrates the changes in lung permeability ($^{125}$I-albumin leakage) in mice following supraceliac aortic cross clamp and treatment with inhibitors of TNF and IL-1.

To determine the effect of visceral ischemia-reperfusion on lung capillary function, 50 mice were anesthetized with pentobarbital, and in 34 animals the supraceliac aorta was cross-clamped for 30 minutes. Eleven of these animals were pretreated with TNF-bp (10 mg/kg) while 9 were pretreated with 150 μg of a monoclonal antibody directed against the murine IL-1 receptor type I (35F5). It has been previously reported that this antibody blocks IL-1 binding to the functional IL-1 type I receptor and attenuates IL-1-mediated inflammation. Control groups consisted of a sham operation group (n=10) and an infrarenal cross-clamp group (n=6). After the removal of the aortic cross-clamps and the onset of reperfusion, the animals were injected with 1 μCi of I$^{125}$ labeled albumin i.v. via the inferior vena cava. At the end of 4 hours of reperfusion the animals were sacrificed and the lungs were treated with bronchoalveolar lavage (BAL) with 1.75 ml of normal saline. The pulmonary mean permeability index was calcuiated as the ratio of CPM/gm BAL over CPM/gm blood. The results are shown in FIG. 4. Both pretreatment with TNF-bp and 35F5 decreased pulmonary capillary injury (p<0.05), with 35F5 having a more pronounced effect.

Thus, these findings demonstrate that the lung injury secondary to supraceliac cross-clamping in the mouse is a result of endogenous production of TNF-α or IL-1. Inhibiting either of these cytokines with novel inhibitors of either TNF-α or the IL-1 type I receptor can minimize the lung injury secondary to visceral ischemia-reperfusion injury.

To demonstrate that similar effects can be obtained by immediate pretreatment with recombinant human IL-10, an additional study was conducted in mice subjected to supraceliac aortic cross-clamping. Visceral ischemia was induced in 90 female C57BL6 mice (20–22 gm) by supraceliac aortic cross-clamping for 25–30 minutes. An additional 38 mice received sham procedures. Plasma IL-10 levels were measured by ELISA at 1, 2, 4 and 8 hrs after reperfusion, and lung neutrophil infiltration was determined by MPO assay at 2 hrs, as previous studies had revealed that maximal neutrophil infiltration occurred in the lung at 2 hrs. Thirty-six of the mice undergoing visceral ischemia-reperfusion were pretreated with 0.2 μg (n=7), 21 μg (n=13), 5 μg (n=6), or 20 μg (n=10) of recombinant human IL-10.

Figure 5:
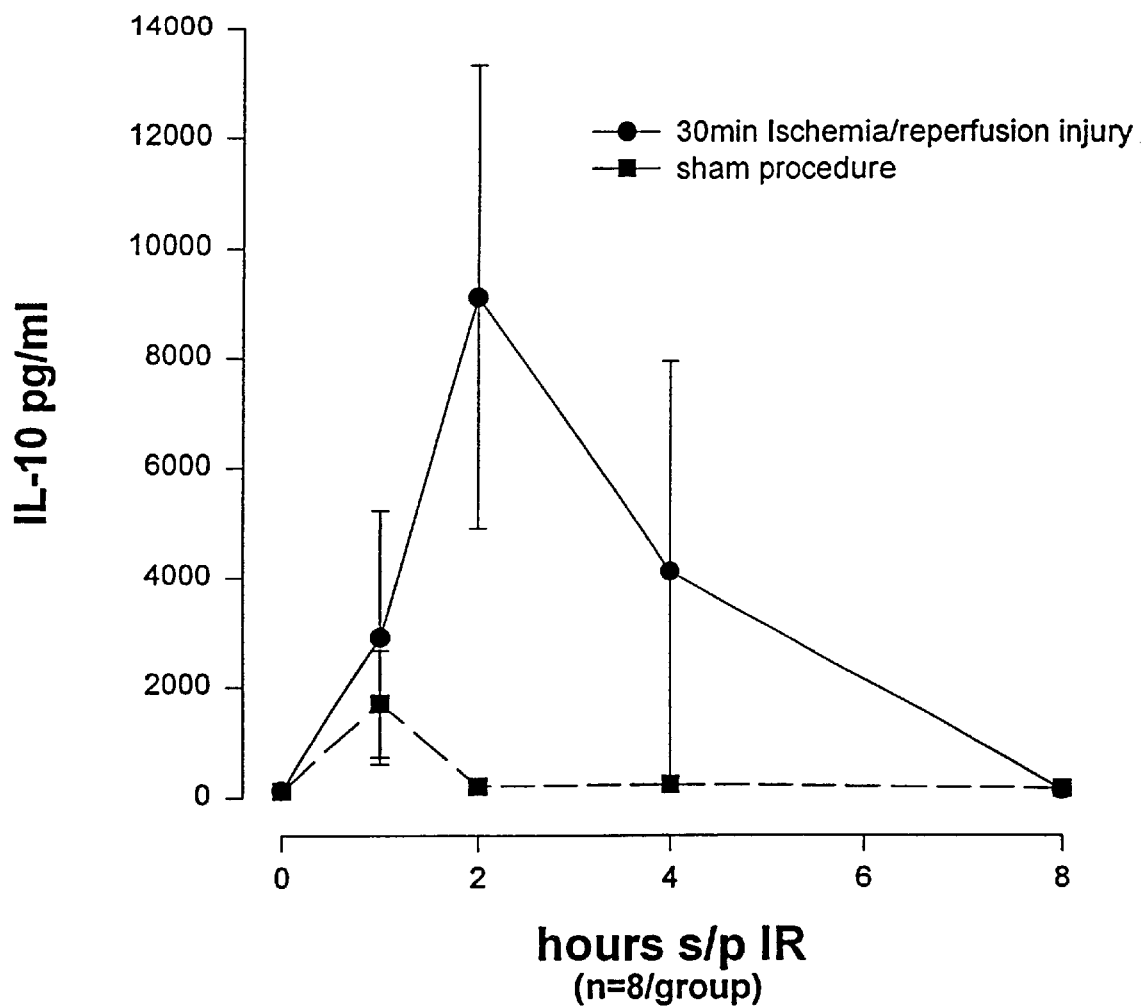
FIG. 5, which illustrates the appearance of IL-10 in the circulation of mice following supraceliac aortic cross clamp used, shows plasma IL-10 concentrations in mice following supraceliac aortic cross-clamping and treatment with recombinant human IL-10.
Figure 6:
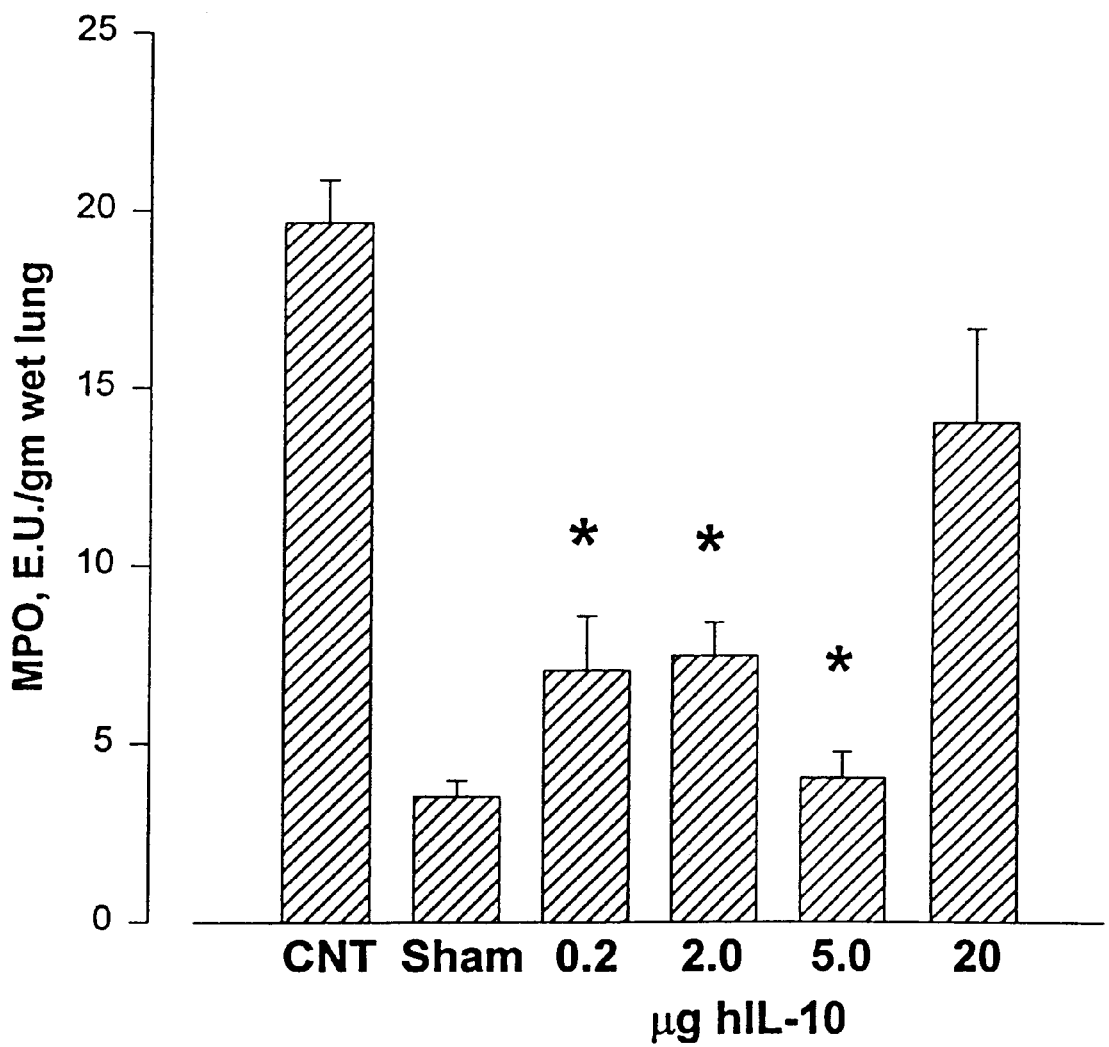
FIG. 6 illustrates the changes in lung myeloperoxidase levels (neutrophil infiltration) in mice following supraceliac aortic cross clamp and treatment with recombinant human IL-10.

Mean plasma IL-10 concentrations peaked at 9,120 pg/ml 2 hours following 25–30 minutes of supraceliac aortic cross-clamping (FIG. 5). Visceral ischemia-reperfusion injury also resulted in an 6-fold increase in lung neutrophil infiltration (p<0.05) (FIG. 6). When mice were pretreated with exogenous IL-10, neutrophil infiltration was significantly reduced (p<0.05 for all doses). Maximal improvements in pulmonary neutrophil infiltration were attained with 5 μg/mouse (250 μg/kg BW) of IL-10.

Visceral ischemia-reperfusion injury associated with supraceliac aortic cross-clamping promotes the release of IL-10, while exogenous IL-10 administration prior to aortic cross-clamping limits pulmonary injury in this model of acute visceral ischemia-reperfusion injury. Thus, exogenous IL-10 may offer a novel therapeutic approach to decrease complications associated with thoracoabdominal aortic aneurysm repair and other ischemia-reperfusion injuries.

Hypothetical Example 3 illustrates a preferred application of the invention contemplated for treating humans.

EXAMPLE 3 (Hypothetical)

A 58 year-old white male presents to the emergency room of a local University hospital complaining of several months of intermittent sharp epigastric and periumbilical abdominal pain, with no other significant symptoms. The patient has no history of any significant medical problems other than a history of atherosclerotic disease. On physical exam, the patient is found to have a nontender, pulsatile mid-abdominal mass, with an audible bruit. Laboratory examination including hematology, biochemistries, liver function tests, urinalysis and amylase are all within normal limits. Flat and upright abdominal x-rays, as well as chest x-rays, are unremarkable. An abdominal CT scan with cuts through the lower chest reveals an aortic aneurysm extending from the level of the diaphragmatic hiatus to the aortic bifurcation, 6.5 cm in largest diameter.

After informed consent is obtained, the patient is prepared for surgery. One hour prior to skin incision, the patient is given a single bolus administration of recombinant human IL-10 at a dose of 10 μg/kg body weight through an indwelling catheter in the median cubital vein. In addition, a lumbar catheter is placed to drain cerebrospinal fluid to maintain intrathecal pressure at 5–10 cm water pressure. Under a general inhalation anesthetic, a left flank incision is made, gaining access to the aorta via a retroperitoneal approach. The diaphragm is divided circumferentially to allow exposure of the thoracic aorta. After the patient is given intravenous doses of mannitol (0.5 gm/kg) and solumedrol (15 mg/kg), the aorta is cross-clamped proximal to the cephalad aspect of the aneurysm and distal to the aortic bifurcation at the level of the proximal external iliac arteries. The aorta is then reconstructed utilizing a bifurcated graft from the level of the caudal thoracic aorta to the external iliac arteries bilaterally. The celiac and superior mesenteric arteries are then sewn to the graft as a Carrel patch. Cross-clamp time and period of warm visceral ischemia is 42 minutes. The aortic cross-clamps are thereafter removed, restoring perfusion of the viscera, pelvis, and lower extremities. Three units of packed red blood cells and two units of fresh frozen plasma are infused. Incisions are then closed, and the patient is transported to the surgical intensive care unit intubated and receiving ventilatory assistance, but hemodynamically stable. After an unremarkable night, the patient is extubated on post-operative day 1. On post-operative day 2, the patient is transferred out of the intensive care unit to the surgical ward. The patient has return of bowel function on post-operative day 5, and is discharged home, ambulating without difficulty, tolerating a regular diet, with his incision healing nicely, with no evidence of infection on post-operative day 7.

Another preferred application of this invention is administration of IL-10 to a patient one to zero hours before the patient receives a major organ transplant. This invention is especially applicable to treatment of ischemia-reperfusion occurring in the visceral section of the body. Regardless of which procedure causes or is expected to cause the ischemia-reperfusion injury, the inventive method of treatment will be deemed successful if one or more of the signs or symptoms of ischemia-reperfusion injury are alleviated or fail to appear at all.

What is claimed is:

1. A method for treating ischemia-reperfusion injury comprising administering to a patient in need of such treatment an amount of IL-10 effective to reduce ischemia-reperfusion injury.

2. A method for preventing or reducing ischemia-reperfusion injury in a patient about to undergo a procedure capable of causing ischemia-reperfusion injury or in a patient who has already undergone such procedure in which ischemia-reperfusion injury has not yet occurred comprising administering to the patient an amount of IL-10 effective to prevent or reduce ischemia-reperfusion injury.

3. The method of claim 1 wherein the ischemia-reperfusion injury was caused by a major organ transplant or repair of an aneurysm.

4. The method of claim 1 wherein the ischemic-reperfusion injury was caused by surgical repair of a thoracic aortic aneurysm, a suprarenal aortic aneurysm, liver, kidney, small intestine, or pancreas transplant, hepatic and biliary surgical resections, total or partial pancreatectomy, total and partial gastrectomy, esophagectomy, colorectal surgery, vascular surgery for mesenteric vascular disease, abdominal insufflation during laparoscopic surgical procedures, blunt or penetrating trauma to the abdomen including gun shot wounds, stab wounds or penetrating wounds or blunt abdominal trauma secondary to deacceleration injury or motor vehicle accidents, hemorrhagic shock due to blood loss, cardiogenic shock due to myocardial infarction or cardiac failure, neurogenic shock or anaphylaxis.

5. The method of claim 2 wherein the procedure expected to cause the ischemia-reperfusion injury is a major organ transplant or repair of an aneurysm.

6. The method of claim 2 wherein the expected cause of the ischemic-reperfusion injury is caused by surgical repair of a thoracic aortic aneurysm, a suprarenal aortic aneurysm, liver, kidney, small intestine, or pancreas transplant, hepatic and biliary surgical resections, total or partial pancreatectomy, total and partial gastrectomy, esophagectomy, colorectal surgery, vascular surgery for mesenteric vascular disease, abdominal insufflation during laparoscopic surgical procedures, blunt or penetrating trauma to the abdomen including gun shot wounds, stab wounds or penetrating wounds or blunt abdominal trauma secondary to deacceleration injury or motor vehicle accidents, hemorrhagic shock due to blood loss, cardiogenic shock due to myocardial infarction or cardiac failure, neurogenic shock or anaphylaxis.

7. The method of claim 1 wherein the amount of IL-10 administered is between 0.1 to 500 $\mu$g/kg of body weight.

8. The method of claim 1 wherein the amount of IL-10 administered is between 1 to 50 $\mu$g/kg of body weight.

9. The method of claim 3 wherein the amount of IL-10 administered is between 0.1 to 500 $\mu$g/kg of body weight.

10. The method of claim 3 wherein the amount of IL-10 administered is between 1 to 50 $\mu$g/kg of body weight.

11. The method of claim 4 wherein the amount of IL-10 administered is between 0.1 to 500 $\mu$g/kg of body weight.

12. The method of claim 4 wherein the amount of IL-10 administered is between 1 to 50 $\mu$g/kg of body weight.

13. The method of claim 2 wherein the IL-10 is administered from one to zero hours before blood flow is re-established and the amount of IL-10 administered is between 0.1 to 500 $\mu$g/kg of body weight.

14. The method of claim 5 wherein the IL-10 is administered from one to zero hours before blood flow is re-established and the amount of IL-10 administered is between 0.1 to 500 $\mu$g/kg of body weight.

15. The method of claim 6 wherein the IL-10 is administered from one to zero hours before blood flow is re-established and the amount of IL-10 administered is between 0.1 to 500 $\mu$g/kg of body weight.

16. A method of treating a hospitalized patient undergoing surgical repair of a thoracic aortic or suprarenal aortic aneurysm comprising administering to said person an amount of interleukin-10 effective to reduce or prevent ischemia-reperfusion injury.

17. A method according to claim 16 wherein the amount of IL-10 administered is between 0.1 to 500 $\mu$g/kg body weight.

18. The method of claim 17 wherein the amount of IL-10 administered is between 1 and 50 $\mu$g/kg body weight.

19. The method of claim 1 wherein the IL-10 is of human or viral origin and is produced biologically from either mammalian cellular sources or by recombinant DNA technology.

20. The method of claim 2 wherein the IL-10 is of human or viral origin and is produced biologically from either mammalian cellular sources or by recombinant DNA technology.

21. The method of claim 16 wherein the IL-10 is of human or viral origin and is produced biologically from either mammalian cellular sources or by recombinant DNA technology.

22. The method of claim 1 wherein the interleukin-10 is administered intravenously, intramuscularly or subcutaneously.

23. The method of claim 2 wherein the interleukin-10 is administered intravenously, intramuscularly or subcutaneously.

24. The method of claim 16 wherein the interleukin-10 is administered intravenously, intramuscularly or subcutaneously.

25. The method of claim 19 wherein the IL-10 is human IL-10.

26. The method of claim 20 wherein the IL-10 is human IL-10.

27. The method of claim 21 wherein the IL-10 is human IL-10.

* * * * *